(12) United States Patent
Georgakoudi et al.

(10) Patent No.: US 7,264,794 B2
(45) Date of Patent: Sep. 4, 2007

(54) METHODS OF IN VIVO CYTOMETRY

(75) Inventors: Irene Georgakoudi, Acton, MA (US); Charles P. Lin, Arlington, MA (US)

(73) Assignee: The General Hospital, Boston, MA (US)

( * ) Notice: Subject to any disclaimer, the term of this patent is extended or adjusted under 35 U.S.C. 154(b) by 99 days.

(21) Appl. No.: 11/016,545

(22) Filed: Dec. 17, 2004

(65) Prior Publication Data

US 2006/0134003 A1 Jun. 22, 2006

(51) Int. Cl.
*A61K 49/00* (2006.01)
(52) U.S. Cl. .................................................... 424/9.1
(58) Field of Classification Search .................. None
See application file for complete search history.

(56) References Cited

OTHER PUBLICATIONS

Michelson et al. Methods 2000;21:259-270.*
Novak et al. Optics Letters 2004;29(1):77-79.*
Momma T, Hamblin MR, Wu HC, Hasan T. Photodynamic therapy of orthotopic prostate cancer with benzoporphyrin derivative: local control and distant metastasis. *Cancer Res* 1998; 58: 5425-31.
Lein M, Koenig F, Misdraji J, et al. Laser-induced hyperthermia in rat prostate cancera; role of site of tumor implantation. *Urology* 2000; 56: 167-72.
Georgakoudi I, Solban N, Novak J, et al. In vivo flow cytometry: A new method for enumerating circulating cancer cells. *Cancer Res* 2004; In Press.
Novak J, Georgakoudi I, Wei X, Prossin A, Lin CP. In vivo flow cytometer for real-time detection and quantification of circulating cells. *Opt Lett* 2004; 29: 77-9.
SEER Cancer Statistics Review, 1975-2001. *In*: L. Ries, M. Eisner, C. Kosary, B. Hankey, B. Miller, L. Clegg, A. Mariotto, E. Feuer, and E. B. (eds). (eds.). Bethesda, MD, http://seer.cancer.gov/csr/1975 2001/: National Cancer Institute, 2004.
Bassan R, Gatta G, Tondini C, Willemze R. Adult acute lymphoblastic leukeamia. *Crit Rev Onc Hematol* 2004; 50: 223-61.
Perelman L, Backman V, Wallace M, et al. Observation of periodic fine structure in reflectance from biological tissue: A new technique for measuring nuclear size distribution. *Phys Rev Let* 1998; 80:627-30.
Shapiro H Practical Flow Cytometry. New York: Alan R. Liss, Inc., 1985.
Handbook of biological confocal microscopy, 2nd edition. New York: Plenum Press, 1995.
Surveillance, Epidemiology and End Results (SEER) Program. National Cancer Institute, 1975-2000.
Cancer Incidence and Survival among Children and Adolescents: United States SEER Program, 1975-1995. National Cancer Institute, 1999.
Hoffman R, Benz E, Shattil S, et al Hematology: Basic Principles and Practice. New York: Churchill Livingstone, 2000.
Smith M, Arthur D, Camitta B, et al. Uniform approach to risk classification and treatment assignment for children with acute lymphoblastic leukemia. *J Clin Oncol* 1996; 14: 18-24.

Coustan-Smith E, Sancho J, Hancock ML, et al. Clinical importance of minimal residual disease in childhood acute lymphoblastic leukemia. *Blood* 2000; 96: 2691-6.
Krauter J, Wattjes MP, Nagel S, et al. Real-time RT-PCR for the detection and quantification of AML1/MTG8 fusion transcripts in t(8;21)-positive AML patients. *Br J Haematol* 1999; 107: 80-5.
Nyvold C, Madsen HO, Ryder LP, et al. Precise quantification of minimal residual disease at day 29 allows identification of children with acute lymphoblastic leukemia and an excellent outcome. *Blood* 2002; 99: 1253-8.
Cave H, van der Werff ten Bosch J, Suciu S, et al. Clinical significance of minimal residual disease in childhood acute lymphoblastic leukemia, European Organization for Research and Treatment of Cancer—Childhood Leukemia Cooperative Group. *N Engl J Med* 1998; 339: 591-8.
Brisco MJ, Condon J, Hughes E, et al. Outcome prediction in childhood acute lymphoblastic leukaemia by molecular quantification of residual disease at the end of induction. *Lancet* 1994; 343: 196-200.
Knechtli CJ, Goulden NJ, Hancock JP, et al. Minimal residual disease status before allogeneic bone marrow transplantation is an important determinant of successful outcome for children and adolescents with acute lymphoblastic leukemia. *Blood* 1998; 92: 4072-9.
Ford AM, Fasching K, Panzer-Grumayer ER, Koenig M, Haas OA, Greaves MF. Origins of "late" relapse in childhood acute lymphoblastic leukemia with TEL-AML1 fusion genes. *Blood* 2001; 98: 558-64.
Konrad M, Metzler M, Panzer S, et al. Late relapses evolve from slow-responding subclones in t(12;21)-positive acute lymphoblastic leukemia: evidence for the persistence of a preleukemic clone. *Blood* 2003; 101: 3635-40.
Potter MN, Steward CG, Oakhill A. The significance of detection of minimal residual disease in childhood acute lymphoblastic leukaemia. *Br J. Haematol* 1993; 83: 412-8.
Venditti A, Buccisano F, Del Poeta G, et al. Level of minimal residual disease after consolidation therapy predicts outcome in acute myeloid leukemia. *Blood* 2000; 96: 3948-52.

(Continued)

*Primary Examiner*—Ralph Gitomer
*Assistant Examiner*—Bin Shen
(74) *Attorney, Agent, or Firm*—William C. Geary, III; Reza Mollaaghababa; Nutter McClennen & Fish LLP

(57) ABSTRACT

The present invention provides methods and systems for performing in-vivo flow cytometry to obtain desired information regarding one or more cell types of interest flowing through a subject's circulatory system. In one embodiment of the invention, a portion of the subject's circulating blood is illuminated with radiation having multiple wavelength components, and the backscattered radiation generated in response to the excitation radiation is detected at a plurality of scattering angles and analyzed to derive the desired information.

14 Claims, 9 Drawing Sheets

OTHER PUBLICATIONS

Coustan-Smith E, Behm FG, Sanchez J, et al. Immunological detection of minimal residual disease in children with acute lymphoblastic leukaemia. *Lancet* 1998; 351: 550-4.

San Miguel JF, Martinez A, Macedo A, et al. Immunophenotyping investigation of minimal residual disease is a useful approach for predicting relapse in acute myeloid leukemia patients. *Blood* 1997; 90: 2465-70.

Janossy G, Bollum FJ, Bradstock KF, Ashley J. Cellular phenotypes of normal and leukemic hemopoietic cells determined by analysis with selected antibody combinations. *Blood* 1980; 56: 430-41.

Coustan-Smith E, Sancho J, Hancock ML, et al. Use of peripheral blood instead of bone marrow to monitor residual disease in children with acute lymphoblastic leukemia. *Blood* 2002; 100: 2399-402.

Facts and Figures. National Institute of Allergy and Infectious Diseases, 2004.

Siddiqua A, Chendil D, Rowland R, et al. Increased expression of PSA mRNA during brachytherapy in peripheral blood of patients with prostate cancer. *Urology* 2002; 60: 270-5.

Fidler I. The pathogenesis of cancer metastasis: the 'seed and soil' hypothesis revisited. *Nature Rev Cancer* 2003; 3: 453-8.

Racila E, Euhus D, Weiss AJ, et al. Detection and characterization of carcinoma cells in the blood. *Proc Natl Acad Sci U S A* 1998; 95: 4589-94.

Dubey P, Su H, Adonai N, et al. Quantitative imaging of the T cell antitumor response by positron-emission tomography. *Proc Natl Acad Sci U S A* 2003; 100: 1232-7.

Dodd SJ, Williams M, Suhan JP, Williams DS, Koretsky AP, Ho C. Detection of single mammalian cells by high-resolution magnetic resonance imaging. *Biophys J* 1999; 76: 103-9.

Naumov GN, Wilson SM, MacDonald IC, et al. Cellular expression of green fluorescent protein, coupled with high-resolution in vivo videomicroscopy, to monitor steps in tumor metastasis. *J Cell Sci* 1999; 112: 1835-42.

Sweeney TJ, Mailander V, Tucker AA, et al. Visualizing the kinetics of tumor-cell clearance in living animals. Proc *Natl Acad Sci U S A* 1999; 96: 12044-9.

Wang W, Wyckoff JB, Frohlich VC, et al. Single cell behavior in metastatic primary mammary tumors correlated with gene expression patterns revealed by molecular profiling. *Cancer Res* 2002; 62: 6278-88.

Padera TP, Kadambi A, di Tomaso E, et al. Lymphatic metastasis in the absence of functional intratumor lymphatics. *Science* 2002; 296: 1883-6.

Bigio I, Bown S, Briggs G, et al. Diagnosis of breast cancer using elastic-scattering spectroscopy: preliminary clinical results. *J Biomed Opt* 2000; 5: 221-8.

Mourant JR, Bigio I, Boyer J, Conn R, Johnson TM, Shimada T. Spectroscopic diagnosis of bladder cancer with elastic scattering spectroscopy. *Lasers Surg Med* 1995; 17: 350-7.

Mourant JR, Bigio I, Boyer J, Johnson TM, Lacey J. Elastic scattering spectroscopy as a diagnostic for differentiating pathologies in the gastrointestinal tract: preliminary testing. *J Biomed Opt* 1996; 1: 1-8.

Sokolov K, Drezek R, Gossage K, Richards-Kortum R. Reflectance spectroscopy with polarized light: is it sensitive to cellular and nuclear morphology? *Opt Express* 1999; 5: 302-17.

Georgakoudi I, Sheets EE, Muller MG, et al. Tri-Modal Spectroscopy for the detection and characterization of cervical pre-cancers in vivo. *Am J Obstet Gynecol* 2002; 186: 374-82.

Georgakoudi I, Jacobson B, Van Dam J, et al. Fluorescence, reflectance and light scattering spectroscopy for evaluating dysplasia in patients with Barrett's esophagus. *Gastroenterol* 2001; 120: 1620-9.

Mourant JR, Canpolat M, Brocker C, et al. Light scattering from cells: the contribution of the nucleus and the effects of proliferative status. *J Biomed Opt* 2000; 5: 131-7.

Mourant JR, Freyer JP, Hielscher AH, Eick AA, Shen D, Johnson TM. Mechanisms of light scattering from biological cells relevant to noninvasive optical-tissue diagnostics. *Appl Opt* 1998; 37: 3586-93.

Mourant JR, Johnson TM, Carpenter S, Guerra A, Aida T, Freyer JP. Polarized angular dependent spectroscopy of epithelial cells and epithelial cell nuclei to determine the size scale of scattering structures. *J Biomed Opt* 2002; 7: 378-87.

Muller MG, Valdez T, Georgakoudi I, et al. Spectroscopic detection and evaluation of morphologic and biochemical changes in early human oral carcinoma. *Cancer* 2003; 97: 1681-92.

Myakov A, Nieman L, Wicky L. Utzinger U, Richards-Kortum R, Sokolov K. Fiber optic probe for polarized reflectance spectroscopy in vivo: Design and performance. *J Biomed Opt* 2002; 7: 388-97.

Gurjar RS, Backman V, Perelman LT, et al. Imaging human epithelial properties with polarized light-scattering spectroscopy. *Nat Med* 2001; 7: 1245-8.

Backman V, Gurjar R, Badizadegan K, et al. Polarized light scattering spectroscopy for quantitative measurement of epithelial cellular structures. *IEEE J Sel Top Quantum Electron* 1999; 5: 1019-26.

Fournier M, Gireau A, Chretien MC, et al. Laboratory evaluation of the Abbott Cell DYN 3500 5-part differential. *Am J Clin Pathol* 1996; 105: 286-92.

Berne BJ, Pecora R Dynamic Light Scattering with Applications to Chemistry, Biology, and Physics Dover (2000). New York: Dover Publications, 2000.

Dunn AK, Bolay H, Moskowitz MA, Boas DA. Dynamic imaging of cerebral blood flow using laser speckle. *J Cereb Blood Flow Metab* 2001; 21: 195-201.

Dunn AK, Devor A, Bolay H, et al. Simultaneous imaging of total cerebral hemoglobin concentration, oxygenation, and blood flow during functional activation. *Opt Lett* 2003; 28: 28-30.

Bolay H, Reuter U, Dunn AK, Huang Z, Boas DA, Moskowitz MA. Intrinsic brain activity triggers trigeminal meningeal afferents in a migraine model. *Nat Med* 2002; 8: 136-42.

Nathan D, Orkin S, Ginsburg D, Look A Hematology of Infancy and Childhood, 6th edition, vol. 2. Philadelphia: WB Saunders Company, 2003.

Calvi LM, Adams GB, Weibrecht KW, et al. Osteoblastic cells regulate the haematopoietic stem cell niche. *Nature* 2003; 425: 841-6.

Cheng T, Rodrigues N, Shen H, et al. Hematopoietic stem cell quiescence maintained by p21cip1/waf1. *Science* 2000; 287: 1804-8

Kiger AA, White-Cooper H, Fuller MT. Somatic support cells restrict germline stem cell self-renewal and promote differentiation. *Nature* 2000; 407: 750-4.

Spradling A, Drummond-Barbosa D, Kai T. Stem cells find their niche. *Nature* 2001; 414: 98-104.

Fidler I. Metastasis: quantitative analysis of distribution and fate of tumor emboli-labeled with $^{125}$I-5-Iodo-2'-deoxyuridine. *J Nat/ Cancer Inst* 1970; 45: 773-82.

Ost V, Neukammer J, Rinneberg H. Flow cytometric differentiation of erythrocytes and leukocytes in dilute whole blood by light scattering. *Cytometry* 1998; 32: 191-7.

Terstappen L, deGrooth B, Visscher K, van Kouterik F, Greve J. Four-parameter white blood cell differential counting based on light scattering measurements. *Cytometry* 1988; 9: 39-43.

de Grooth B, Terstappen L, Pupples G, Greve J. Light-scattering polarization measurements as a new parameter in flow cytometry. *Cytometry* 1987; 8: 539-44.

Terstappen L, de Grooth B, ten Napel C, van Berkel W, Greve J. Discrimination of human cytotoxic lymphocytes from regulatory and B-lymphocytes by orthogonal light scattering. *J Immunol Methods* 1986; 95: 211-6.

Often G, Loken M. Two color light scattering identifies physical differences between lymphocyte subpopulations. *Cytometry* 1982; 3: 182-7.

Backman V, Gopal V, Kalashnikov M, et al. Measuring cellular structure at submicron scale with light scattering spectroscopy. *IEEE J Sel Top Quantum Electron* 2001; 7: 887-93.

Streekstra G, Hoekstra A, Nijhof E-J, Heethaar R. Light scattering by red blood cells in ektacytometry:Fraunhofer versus anomalous diffraction. *Appl Opt* 1993; 32: 2266-72.

Handin R, Lux S, Stossel T Blood: Priniciples and Practice of Hematology, 2nd edition. Philadelphia: Lippincott Williams and Wilkins, 2002.

Huberty C Applied Discriminant Analysis. New York: Wiley, 1994.

Borenstein J, Terai H, King K, Weinberg E, Kaazempur-Mofrad M, Vacanti J. Microfabrication technology for vascularized tissue engineering. *Biomedical Microdevices* 2002; 4:3: 167-75.

Kaihara S, Borenstein J, Koka R ea. Silicon micromachining to tissue engineer branched vascular channels for liver fabrication. *Tissue Eng* 2000; 6: 105-17.

Wulf G, Luo K, Goodell M, Brenner M. Anti-CD45-mediated cytoreduction to facilitate allogeneic stem cell tranplantation. *Blood* 2003; 101: 2434-39.

Groner W, Winkelman J, Harris A. Orthogonal polarization spectral imaging: A new method for study of the morocirculation. *Nat Med* 1999; 5: 1209-13.

Muller MG, Wax A, Georgakoudi I, Dasari R, Feld MS. A reflectance spectrofluorimeter for real-time spectral diagnosis of disease. *Rev Sci Instrum* 2002; 73: 3933-7.

Uckun FM, Manivel C, Arthur D, et al. In vivo efficacy of B43 (anti-CD19)-pokeweed antiviral protein immunotoxin against human pre-B cell acute lymphoblastic leukemia in mice with severe combined immunodeficiency. *Blood* 1992; 79: 2201-14.

Ek O, Gaynon P, Zeren T, Chelstrom LM, Myers DE, Uckun FM. Treatment of human B-cell precursor leukemia in SCID mice by using a combination of the anti-CD19 immunotoxin B43-PAP with the standard chemotherapeutic drugs vincristine, methylprednisolone, and L-asparaginase. *Leuk Lymphoma* 1998; 31: 143-9.

Wang JH, Doyle M, Manning BJ, et al. Cutting edge: bacterial lipoprotein induces endotoxin-independent tolerance to septic shock. *J Immunol 2003*; 170: 14-8.

\* cited by examiner

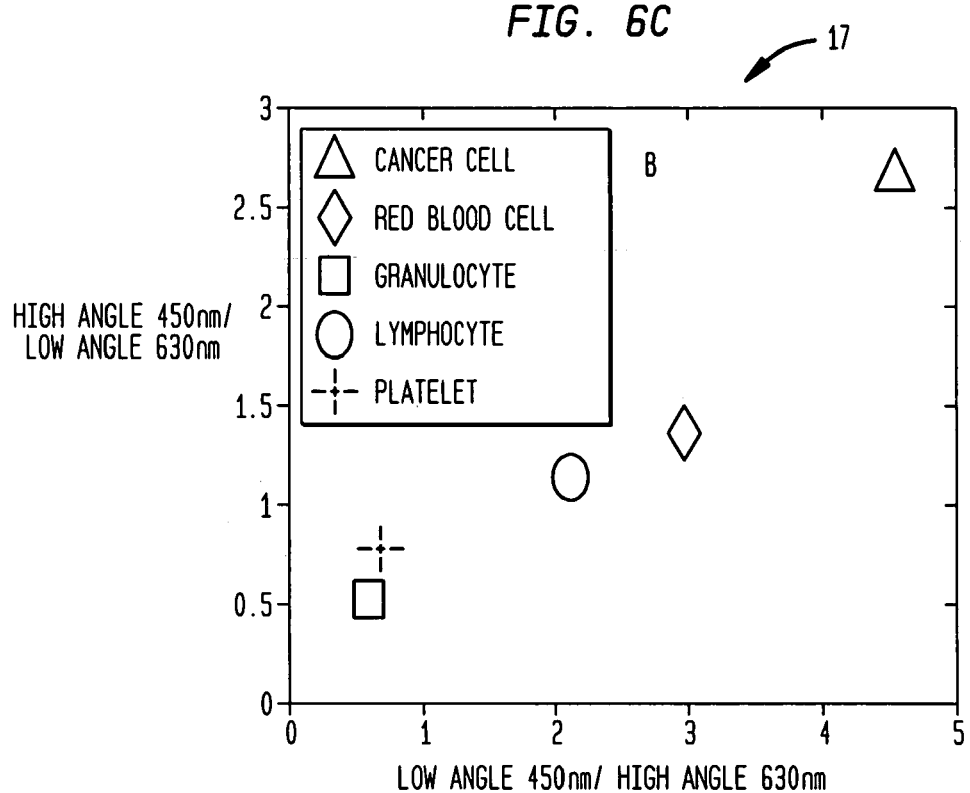
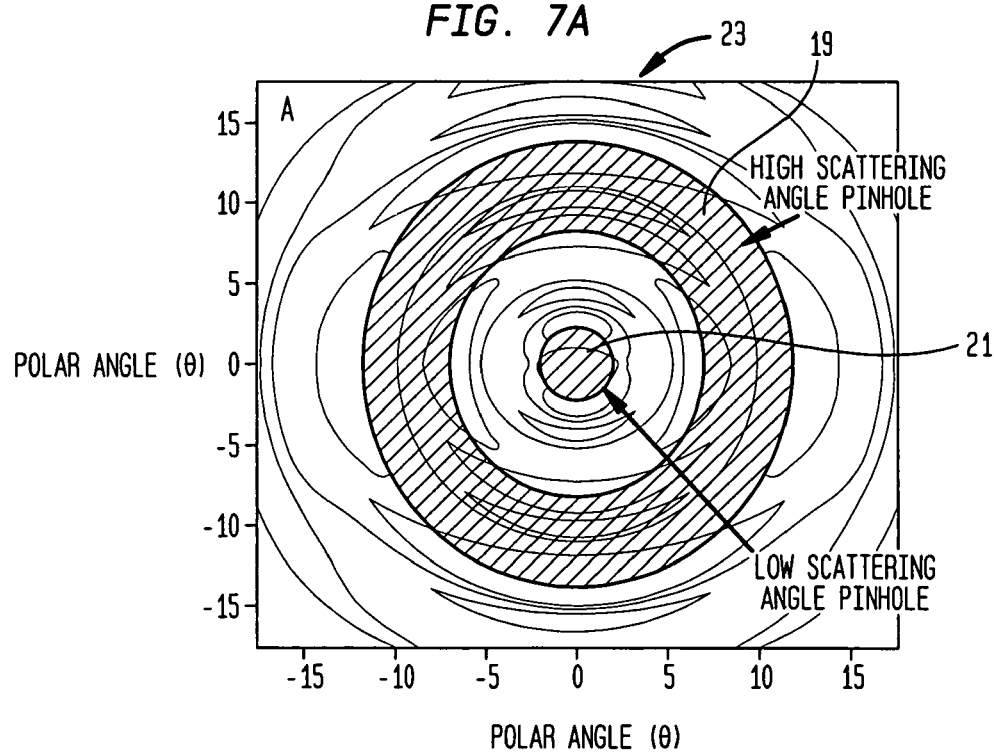

METHODS OF IN VIVO CYTOMETRY

BACKGROUND OF THE INVENTION

The present invention relates generally to methods and systems for performing in-vivo flow cytometry, and more particularly, to methods and systems for performing non-invasive in-vivo flow cytometry.

Conventional flow cytometric techniques known in the art for detecting and/or quantifying desired cell types flowing through a subject's circulatory system typically require extraction of blood from the subject followed by labeling and ex-vivo detection. For example, in standard ex-vivo flow cytometry, cells present in a blood sample, drawn from a subject, are fluorescently labeled, and passed in a single file through a flow stream to be interrogated by a light source so as to derive cytometric information. In another ex-vivo conventional technique, known as hemocytometry, cells are counted against a grid while being viewed with a microscope to determine cell types and numbers.

Such ex-vivo techniques, however, suffer from a number of shortcomings. For example, each measurement provides only a single time sample. Consequently, it is difficult to use these techniques to obtain a reliable temporal cell population profile for a cell type of interest that varies unpredictably or rapidly with time. Further, such conventional techniques can suffer from a significant time delay between sample collection and analysis, which can potentially lead to measurement inaccuracies.

Some in-vivo techniques for detection of static and circulating fluorescently-labeled cells are also known. Many of these techniques, however, show difficulty, or simply fail, in tracking cells flowing at a high velocity, especially in the arterial circulation, even when they capture images at video rates. In addition, in many of such techniques, extracting quantitative information from acquired data may be tedious. Moreover, in some cases, fluorescent probes for labeling a cell type of interest may not be available.

Hence, there is a need for enhanced methods and systems for performing in-vivo flow cytometry.

SUMMARY OF THE INVENTION

In one aspect, the present invention provides a method of performing in-vivo flow cytometry that includes illuminating in-vivo a portion of a subject's circulating blood containing at least a cell type of interest with radiation having at least one selected wavelength component. By way of example, the wavelength component can be in a range of about 450 nm to about 1000 nm. The term "radiation" and "light" are herein utilized interchangeably, and generally refer to radiation not only in the visible portion of the electromagnetic spectrum but in any desired portion, such as the infrared. The radiation backscattered from the illuminated blood is measured at at least one angular location, and preferably at two or more different angular locations. The detected backscattered radiation is analyzed to identify and derive selected information regarding the cell type of interest, such as an absolute or a relative cell count. The term "backscattered radiation" is known in the art. To the extent that any further explanation may be needed, it refers to scattered radiation propagating in directions that are generally opposite to the propagation direction of the excitation direction. A backscattered direction can be exactly opposite to the propagation direction. Alternatively, a backscattered propagation direction can form a non-zero angle (less than about 90 degrees) relative to the excitation direction. In many cases, the backscattered radiation is substantially contained within a solid angle whose central axis is formed by a direction exactly opposite to that of the excitation radiation.

The detected backscattered radiation can be analyzed to differentiate a cell type of interest, for example, red blood cells, white blood cells, thrombocytes, epithelial cells or particular cancer cells, from other cell types present in the illuminated blood. Further, the measured intensity of the detected backscattered information can be analyzed to provide information regarding this cell type, such as, its relative count. The information can also indicate the presence and/or progression of a disease or the progress of an applied treatment protocol.

In a related aspect, the detection of the backscattered radiation is preferably performed confocally with respect to an imaging plane that includes a blood vessel illuminated by excitation radiation.

In another aspect, the invention provides a method of performing in-vivo flow cytometry by illuminating in-vivo a portion of a subject's circulating blood with radiation having at least two selected wavelength components. For each wavelength component, the intensity of the backscattered radiation from the illuminated blood can be measured at two or more angular locations. The intensity measurements can then be analyzed to derive information, such as, cell type or cell count, of one or more cell types of interest present in the subject's circulating blood.

In a related aspect, one of the wavelength components is selected to lie within a spectral region that is associated with low hemoglobin absorption and another wavelength is selected to lie within a spectral region associated with high hemoglobin absorption.

The subject's blood can be illuminated with the two or more wavelength components simultaneously, or separately in different time intervals. Further, at least one of the angular locations can be selected to lie within a circular strip in a plane of backscattered radiation, which is defined by two polar angles relative to the central axis of the backscattered radiation and by two azimuthal angles defined in that plane.

In yet another aspect, the invention provides a method for in-vivo detection and quantification of a cell type of interest present in a subject's circulatory system that includes illuminating in-vivo a subject's circulating blood with radiation having multiple wavelength components (e.g., wavelengths in a range of about 450 nm to about 1000 nm), and detecting radiation backscattered from the illuminated blood at two or more angular locations having different scattering angles relative to a central axis of the backscattered radiation. The detected radiation can be analyzed as a function of wavelength and scattering angle to derive selected information regarding the cell type of interest.

The analysis of the detected backscattered radiation can include, for example, differentiating spectral signatures of a cell type of interest from those of other cells present in the subject's circulatory system. Such differentiation can be achieved, for example, by comparison of detected intensities at one angular region with those at another angular region, as well as, similar comparison relative to wavelengths.

In a related aspect, one of the angular regions includes locations forming polar angles in a range of about zero to about 5 degrees relative to the backscattering central axis, and another angular region includes locations forming polar angles in a range of about 5 to about 10 degrees. These angular regions can be further defined by azimuthal angles ranging, for example, from about zero to about 90 degrees, from about zero to about 180 degrees, or from about zero to about 360 degrees.

In a further aspect, the invention provides a system for performing in-vivo flow cytometry in a live subject, which includes a radiation source for generating radiation having multiple wavelength components, and an optical system for focusing the radiation onto a focal plane so as to illuminate a portion of the subject's blood flowing through a vessel that is at least partially disposed in that focal plane. The system can also include a detector optically coupled to the focal plane for detecting radiation backscattered from the subject's blood in response to the excitation radiation at a plurality of scattering angles, and an analysis module that operates on the detected backscattered radiation to derive selected information regarding a cell type of interest present in the subject's blood based on intensities of the backscattered radiation at scattering wavelengths corresponding to the excitation wavelengths and the plurality of the scattering angles. For example, the analysis module can compare the backscattered intensity at at least one wavelength and one scattering angle with the backscattering intensity at another scattering angle, either corresponding to the same wavelength or corresponding to a different excitation wavelength, to derive the desired cytometric information, e.g., an absolute or a relative cell count.

In another aspect, the invention provides a system for performing in-vivo flow cytometry in a live subject includes two radiation sources generating radiation with at least two different wavelength components. An optical system coupled to these radiation sources can direct these wavelength components onto a focal plane so as to illuminate in-vivo a portion of blood circulating in a subject's vessel that is positioned at least partially in the focal plane. The system further includes one or more detectors that are positioned so as to detect, at at least two separate scattering angles, radiation backscattered from the subject's circulating blood in response to illumination, and an analysis module that operates on the detected backscattered radiation to derive selected information regarding one or more cell types of interest present in the subject's blood.

BRIEF DESCRIPTION OF THE DRAWINGS

FIG. 7A illustrates another simulated backscattered intensity map in which two annular angular regions are selected for comparison of integrated intensity data.

DETAILED DESCRIPTION

The present invention provides methods and systems for performing in-vivo flow cytometry in a live subject to obtain desired information regarding one or more cell types of interest, for example, a relative count of these cell types. As discussed in more detail below, in many embodiments of the invention, a portion of a subject's circulating blood is illuminated with radiation having one or multiple wavelength components, and the backscattered radiation generated in response to the excitation radiation is detected at a plurality of scattering angles, and analyzed to derive the desired information.

Figure 1:
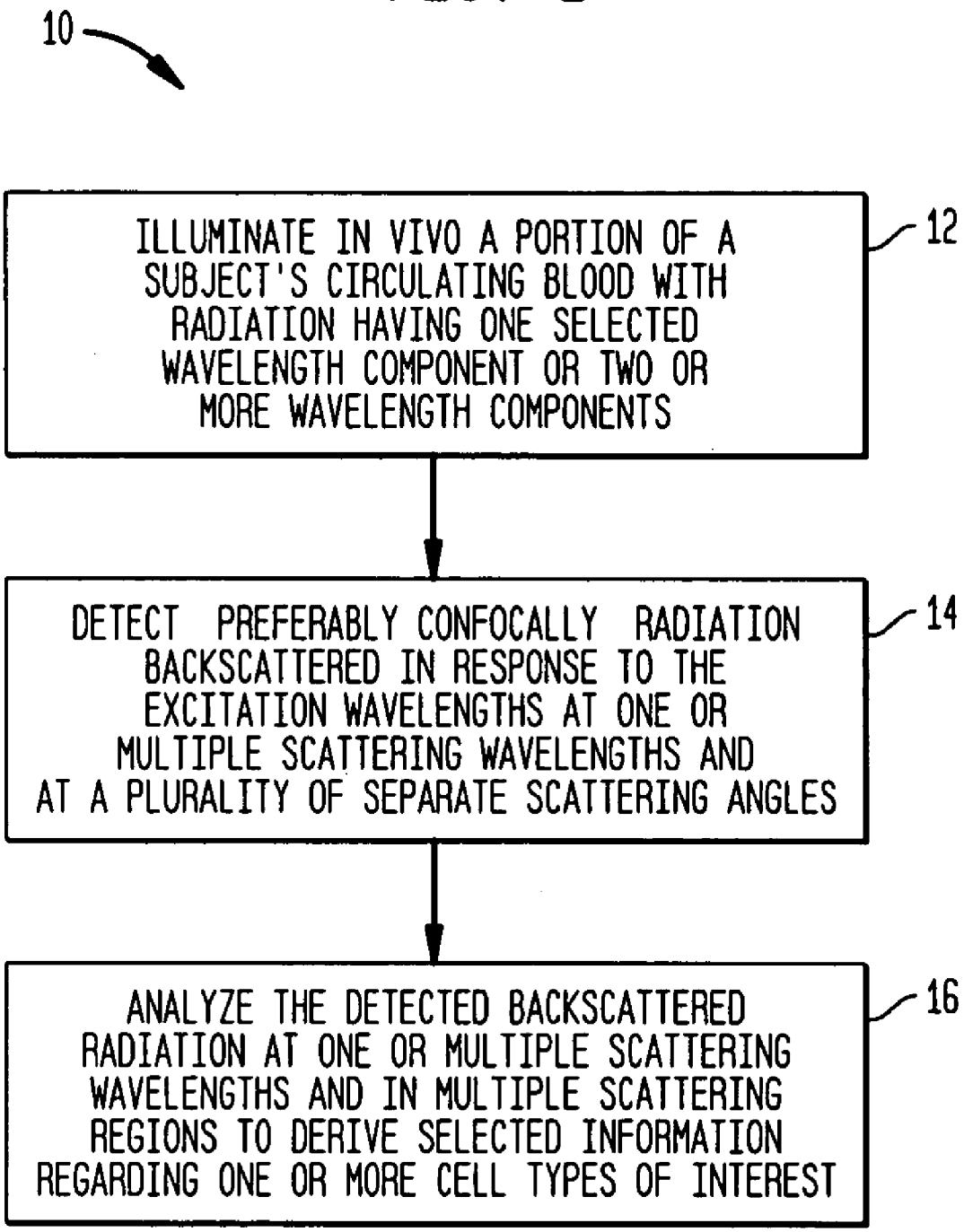
FIG. 1 is a flow chart depicting various steps in one exemplary embodiment of a method according to the teachings for the invention for performing in-vivo flow cytometry, FIG. 2 schematically illustrates an exemplary apparatus according to one embodiment of the invention for performing in-vivo flow cytometry.

More specifically, with reference to a flow chart 10 of FIG. 1, in one embodiment of the method of the invention for performing in-vivo cytometry, in an initial step 12, a portion of a subject's circulating blood is illuminated with radiation having at least one wavelength component, and more preferably two or more wavelength components. For example, an illuminating radiation beam can be directed to subject's vessel so as to traverse a stream of cells flowing in that vessel. When multiple wavelength components, rather than a single wavelength component, are utilized, the illumination at these wavelengths can be performed simultaneously, or in separate temporal intervals. For example, radiation from two sources, each generating one wavelength of interest, can simultaneously impinge on the circulating blood. Alternatively, the circulating blood can be illuminated with two wavelength components in two separate time intervals, for example, by utilizing a single broadband source that can be coupled to two or more filters to generate wavelength components of interest. In another embodiment, a broadband generating two or more wavelength components can be employed for simultaneous illumination of the circulating blood with those wavelength components. In some embodiments, the illuminating wavelengths are selected to be in a range of about 450 nm to about 1000 nanometers, and more preferably, in a range of about 450 nm to about 700 nm.

The term wavelength component as used herein can refer to a single wavelength or a wavelength band centered relative to a wavelength. Such a wavelength band can be centered about a selected wavelength and can have a width in a range of about 1 to about 40 nm. In many embodiments of the invention, two or more illumination wavelengths are selected to correspond to different hemoglobin absorption coefficients to primarily enhance contrast in the backscattered data between radiation scattered by red blood cells relative to other cell types. For example, one illumination wavelength component can be selected to be about 420 nm, or in the range of about 540 nm to 580 nm, at which hemoglobin exhibits a relatively high absorption coefficient, while another wavelength component can be selected to be in a range of about 600 nm to about 635 nm, at which hemoglobin exhibits a lower absorption coeffcient.

In many embodiments of the invention, blood vessels that are readily accessible, for example, vessels along a subject's arms and legs, are employed for illuminating blood flowing therethrough. Preferably, such vessels are selected to be those located in areas of the skin that exhibit limited keratinization and melanin absorption to inhibit degradation of the signal-to-noise (S/N) ratio. By way of example, a subject's eye blood vessels can be employed for practicing the methods of the invention. In such a case, care may be taken to minimize eye movement and/or limit the data acquisition time so as to ameliorate the degradation effects of the eye movement on the acquired data.

Referring again to the flow chart 10, in step 14, radiation backscattered from the illuminated blood is detected at one, or two or more of the scattering wavelengths corresponding to the illuminating wavelengths and in two or more scattering regions. For example, the backscattered radiation at two or more wavelengths is detected at multiple scattering angles. In general, detected backscattered radiation is caused by elastic scattering in which the scattering wavelength is the same as the excitation wavelength. The detection of the backscattered radiation is preferably performed confocally relative to the illumination. The term "confocal detection" is known in the art, and to the extent that any further explanation may be required, it refers to detecting the backscattered radiation in a plane that is optically conjugate relative to a plane of the illumination radiation that is directed to the subject's vessel to illuminate circulatory cells.

In a subsequent step 16, the intensity of the backscattered radiation, detected at one, or at a plurality of different wavelengths, and in different scattering regions, is analyzed to derive selected information regarding one or more cell types of interest. For example, the wavelength and the angular dependence of the detected backscattered radiation can be employed as a unique signature of the cell type of interest to derive the desired information. Such information can include, for example, differentiation of the cell type relative to other cell types present in the subject's blood, a relative or an absolute count of that cell type.

As discussed in more detail below, the analysis of the measured backscattered intensity can rely on different expected backscattered intensity profiles associated with different cell types. In particular, different morphologies and/or internal structures of different cell types (and different surface proteins) can lead to varying backscattered intensity profiles. Such differences can be utilized in comparing measured backscattered intensity in one angular region with that in at least another angular region to determine contribution of one or more cell types to the measured backscattering intensity profile. In addition, comparison of the backscattered intensity at one excitation wavelength with that corresponding to a different excitation wavelength can facilitate resolution of the backscattered intensity data into contributions from different cell types.

The methods of the invention, such as those described above, for performing in-vivo flow cymometery provide a number of advantages. In particular, they are non-invasive and do not require blood sample removal or cellular staining. They are painless and can provide quantitative results in real-time. As such, they can be employed in both basic research and clinical applications for frequent or continuous monitoring of a subject's blood constituents to detect, for example, rare events (e.g., circulating cancer cells). Further, such a non-invasive technique can be well suited for particular patient population groups, such as pediatric patient populations. In particular, children have numerous superficial blood vessels along their arms, legs, feet and forehead, which can be easily accessible for illumination with light having suitable wavelength components. In addition, drawing blood samples from children, required by conventional methods, is typically technically difficult because of the small size of children's veins and can be physically painful and emotionally stressful for the children and their parents.

Figure 2:
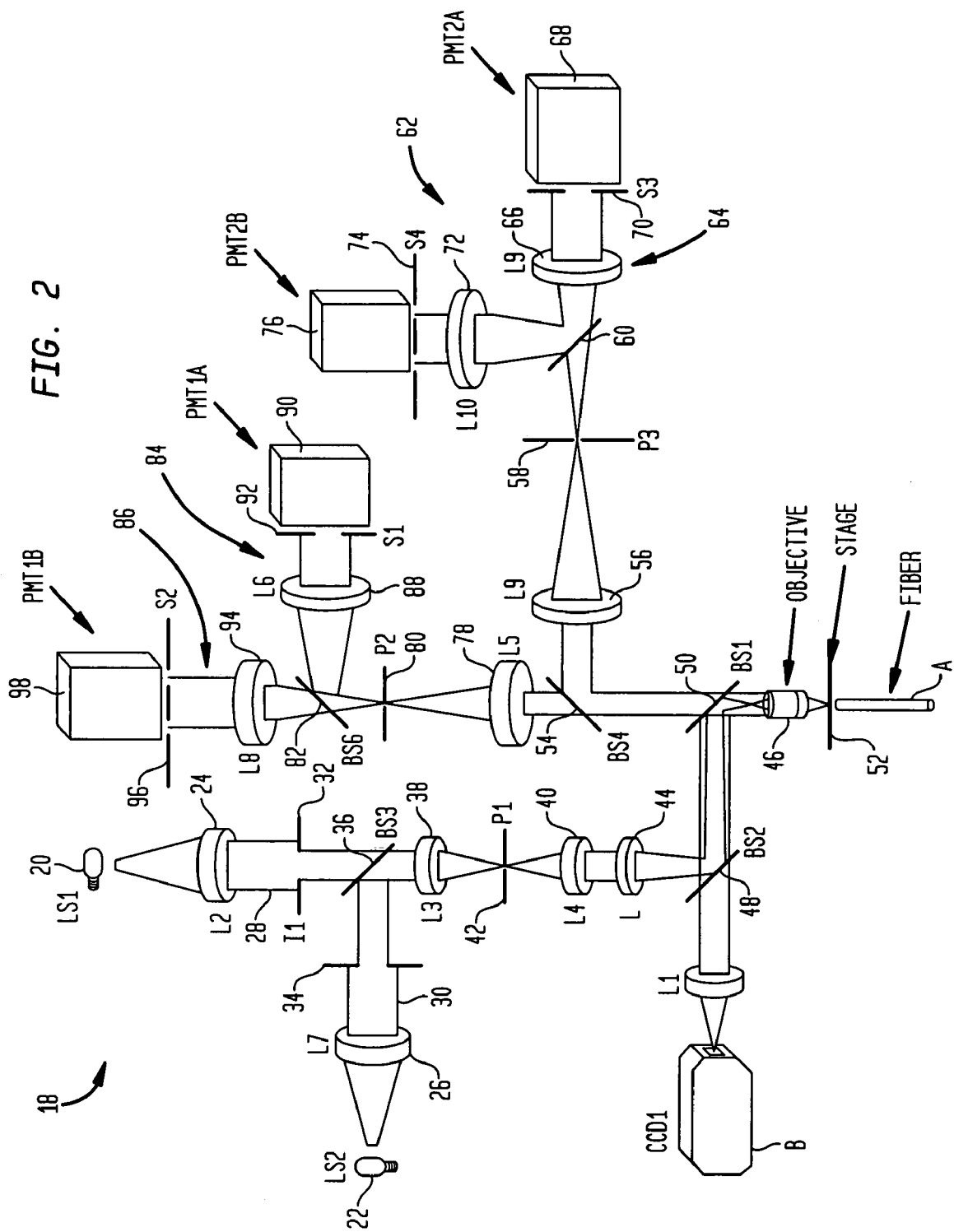

FIG. 2 schematically illustrates an exemplary apparatus 18 according to the teachings of the invention for performing flow cytometry, and more specifically, an apparatus for implementing the methods of the invention, such as those described above, for performing flow cytometry. The exemplary apparatus 18 includes two radiation sources 20 and 22 that generate radiation in two separate wavelength regions. These separate wavelength regions can be disjointed or partially overlapping. In some embodiments, the radiation generated by one source can include wavelength components corresponding to a spectral region in which hemoglobin exhibits a relatively high absorption coefficient and the radiation generated by the other source can include wavelength components corresponding to a spectral region in which hemoglobin exhibits a lower absorption coefficient. By way of example, in some embodiments, one radiation source generates radiation having wavelength components in a range of about 540 to about 580 nm while the other source generates radiation having wavelength components in a range of about 600 nm to about 633 nm.

The radiation sources 20 and 22 can generate coherent or incoherent radiation. Without any limitation, some examples of incoherent sources suitable for use in the exemplary apparatus 18 include high power Xe and Hg lamps, superluminescent diodes, while some examples of suitable coherent sources include ion and solid state lasers, such as, HeNe, diode and Ar lasers. In embodiments in which one or both of the radiation sources are lasers, an optical diffuser (not shown here) may be employed to diffuse the laser light so as to minimize laser speckle, which may degrade the light scattering signal-to-noise (S/N) ratio.

With continued reference to FIG. 2, two lenses 24 and 26 collimate radiation emitted by the sources 20 and 22, respectively, to generate two collimated beams 28 and 30 that pass through irises 32 and 34 to reach a dichroic beam splitter 36. The dichroic beam splitter 36 allows the radiation from the source 20 to pass through while reflecting the radiation from the source 22 in a direction that is substantially co-linear with that of the radiation from the source 20 to generate an excitation beam containing wavelength components from both sources. Achromats 38 and 40, together with a pinhole 42, provide spatial filtering of the co-propagating radiation beams from sources 20 and 22. More specifically, the pinhole 42 is positioned such that its distance from each of the achromatic lenses 38 and 40 is substantially equal to the focal length of that lens. Hence, the achromat 38 focuses the collimated radiation beam that it receives onto the pinhole 42 and the achromat 40 directs the radiation emanating from the pinhole 42 as a collimated beam towards another achromat 44, which in turn focuses the radiation beam at the back focal plane of an objective lens 46. More particularly, in this embodiment, two beam splitters 48 and 50 reflect the radiation received from the lens 44 toward the objective lens 46, which in turn collimates the radiation beam for illuminating a selected subject's vessel positioned, and preferably fixated, on a stage 52. More particularly, the radiation illuminates in-vivo blood flowing through the subject's vessel. In some embodiments in which the radiation sources 20 and 22 provide well-collimated radiation beams, spatial filtering by the pinhole 42, together with the achromats 38 and 40, may not be required. In some embodiments of the invention, a vessel of interest can be identified by illuminating tissue containing that vessel by radiation from a source A (e.g., a ligh-emitting diode) and imaging the transmitted radiation by a lens L1 onto another CCD camera B.

With continued reference to FIG. 2, a portion of the radiation backscattered, i.e., radiation scattered substantially towards the objective lens 46, from the illuminated circulating blood is transmitted through the beam splitter 50 to a detection arm of the exemplary apparatus 18. More specifically, the backscattered radiation in a wavelength region, i.e., having wavelength components, associated with scattering caused by the radiation source 20 is transmitted through the beam splitter 50 towards a dichroic beam splitter 54 that reflects this backscattered radiation towards an achromat 56, which in turn focuses the radiation onto a pinhole 58 for spatial filtering. The backscattered radiation emanating from the pinhole 58 is split by a beam splitter 60 into two detection paths 62 and 64. For example, the radiation can be split equally between the two detection paths. The radiation propagating in the detection path 64 is collimated by a lens 66 and is directed to a detector 68, for example, a photomultiplier tube (PMT). A spatial detection filter 70 is placed in the back focal plane of the lens 66 and in front of the detector 68 to allow the backscattered radiation within a selected angular region to reach the detector while blocking the backscattered radiation in other angular regions. For example, in this exemplary embodiment, the spatial filter 70 can allow the backscattered radiation propagating in directions having polar angles relative to a central axis of propagation in a range of zero to about 5 degrees to reach the detector. The spatial filter can be chosen to be circularly symmetric to permit, for each polar angle of interest, radiation corresponding to azimuthal angles ranging from zero to 360 degrees to be detected by the photomultipler tube 68

In a similar fashion, the backscattered radiation propagating along the detection path 62 is directed by a lens 72 onto a different spatial filter 74 that allows radiation in an angular region, different that that defined by the spatial filter 70, to reach another detector 76, e.g., another photomultiplier tube. For example, the angular region defined by the spatial filter 74 can correspond to polar angles ranging from about 5 degrees to about 12 degrees. In this manner, the intensity of the backscattered radiation in wavelength regions corresponding to the scattered radiation caused by the source 20 is detected in two separate angular regions. Although in this embodiment, the angular regions corresponding to the spatial filters 70 and 74 are disjointed, in other embodiments, the angular regions can be partially overlapping.

The backscattered radiation in a wavelength region corresponding to scattering caused by the other radiation source 22 is transmitted through the dichroic beam splitter 54 to a lens 78 that focuses the radiation onto a pinhole 80. A beam splitter 82 transmits a portion of the radiation emanating from the pinhole 80 (typically about 50% of the radiation) into a detection path 84, and the rest of the radiation into another detection path 86. The radiation propagating through the detection path 84 is directed by a lens 88 onto a detector 90, e.g., a photomultiplier tube (PMT), in front of which a detection angular spatial filter 92 is placed. The spatial filter 92 allows radiation within a selected angular region to reach the detector while blocking radiation in other angular regions. In this exemplary embodiment, the spatial filter 92 allows radiation within an angular region defined by polar angles in a range of zero to about 5 degrees, or more preferably in a range of zero to about 3 degrees, to reach the detector. In a similar fashion, the scattered radiation propagating through the detection path 86 is directed by a lens 94 through an angular spatial filter 96 onto a detector 98, e.g., a photomultiplier tube. The spatial filter 96 is selected to allow passage of the backscattered radiation within an angular region different than that defined by the spatial filter 92. For example, in this embodiment, the spatial filter 96 selects backscattered radiation in an angular region substantially confined by polar angles 5 and 12 to be detected by the photomultiplier tube 98.

In many embodiments of the above exemplary apparatus 18, each of the pinholes 58 and 80 is confocally positioned relative to the focal plane of objective 46. That is, each pinhole 58 and 80 is positioned in an optically conjugate plane relative to the focal plane of objective 46. In other words, only those scattered photons that substantially originate from illuminated blood in the image plane of the excitation pinhole 42 are imaged onto the pinholes 58 and 80. This allows efficiently detecting scattered radiation emitted from a selected excitation volume while minimizing detection of interfering photons that may originate beyond this volume. The confocal detection scheme ensures that such interfering photons, even if they reach the detection plane, will not be generally in focus in that plane. In other words, the confocal arrangement substantially eliminates detection of radiation from out-of-focus scattering sources.

In other embodiments, rather than utilizing a combination of spatial filters and two photomultiplier tubes to collect light over two distinct scattering angle regions, multi-anode photomultiplier tubes (PMT) can be employed. Such multi-anode PMT's, which could serve essentially as low resolution CCDs, can provide automatic spatial filtering with different parts of the PMT detector corresponding to different scattering angles.

Figure 3:
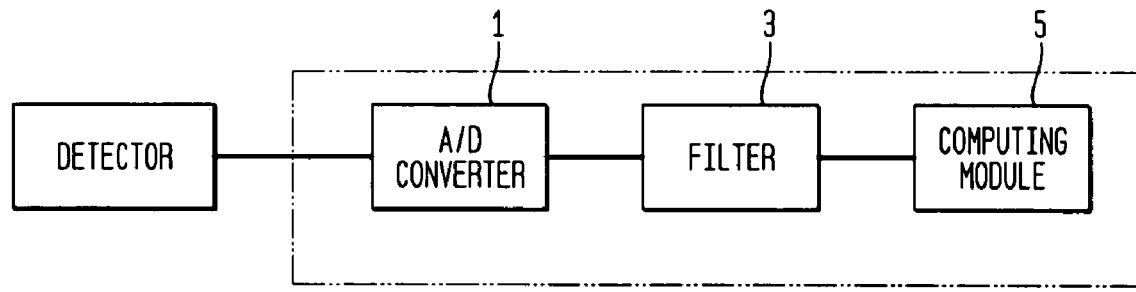
FIG. 3 is a schematic diagram of one exemplary analysis module of the apparatus of FIG. 2 for analyzing collected scattering data, FIG. 4 schematically depicts formation of an intensity map on an image plane by radiation backscattered from a subject's illuminated blood.

With reference to FIG. 3A, scattered radiation intensity detected by the photomultiplier tubes 68, 76, 90 and 98 can be transmitted to an analysis module 100 for analysis and/or storage. The exemplary analysis module 100 can include an analog-to-digital (A/D) converter 1 that digitizes the signal received from the detector, and a filter 3 that operates on the digital signal to provide filtering of the data. For example, the filter can employ a moving average window having a width selected to substantially remove high frequency noise. In some embodiments, the filter can be a digital signal processing unit (DSP) that can provide digital filtering of the data. The analysis module further includes a computing module 5 that can apply analysis methods according to the teachings of the invention to the filtered data to derive desired cytometric information. The computing module can also include storage capability for storing the data, and a display unit for displaying the data and/or the analysis results.

Figure 4:
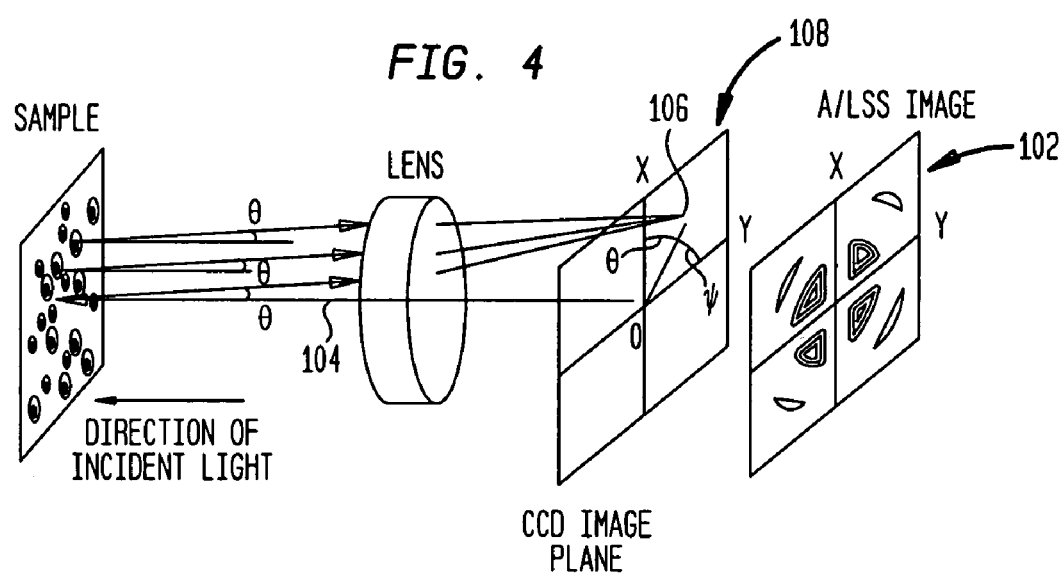

The data corresponding to each photomultiplier tube can be represented as an angular intensity map for a selected wavelength component or wavelength region associated with radiation scattered from the circulating blood in response to excitation radiation. By way of example and only for illustrative purposes, FIG. 4 schematically depicts such an angular intensity map 102 corresponding to radiation propagating in backscattered directions forming scattering angles in a selected range relative to a central optic axis 104, e.g., relative to the axis of the excitation radiation, between two selected values. For example, the intensity on the image at point 106 on an image plane 108 corresponds to substantially parallel backscattered radiation rays that leave the illuminated sample with similar scattering angles (polar angle $\theta$ and azimuthal angle $\phi$ relative to the central axis 104).

The analysis of the scattering data can provide information regarding one or more selected cell types of interest. For example, differential detection of scattered light within low and high scattering angle regions, can provide information about the size and texture of nuclei and smaller organelles, respectively. For example, intensity variations within small scattering angles, e.g., angles in a range of about 0 (zero) to about 5 degrees, can be most sensitive to particles that are large relative to the excitation wavelength, such as nuclei whose sizes are about 10 to 40 times larger than the illumination wavelength. For example, a red blood cell has a typical diameter of approximately 8 microns ($\mu$m) and lacks a nucleus while a lymphocyte is about 10 microns in diameter and has a relatively spherical nucleus that occupies almost the entire cell. Neutrophils are about 10-14 microns in diameter and contain significant number of finer granules in their cytoplasm and nuclei having characteristic irregular shapes consisting of 2-5 lobes. In contrast, monocytes are larger cells that are about 15-22 microns across with nuclei of various shapes. Eosinophils are typically larger than neutrophils and have nuclei with two lobes, and include granules within the cytoplasm with refractile properties. And basophils are smaller than neutrophils and have nuclei with two lobes and cytoplasmic granules that are fewer in number and are less regular than those corresponding to eosinophils. Hence, in many embodiments of the invention, the scattering signal in smaller angular ranges, e.g., a range of about 0 to about 5 degrees, can be analyzed for differentiating among different cell types based on larger morphological differences, such as cell size and presence or lack of nucleus. And the backscattered radiation corresponding to larger scattering angles, e.g., scattering angles in a range of about 5 to about 25 degrees, can be analyzed to search for smaller morphological features, such as granules within cytoplasm, to facilitate detection and characterization of cell types giving rise to the observed intensity features.

Figure 5:
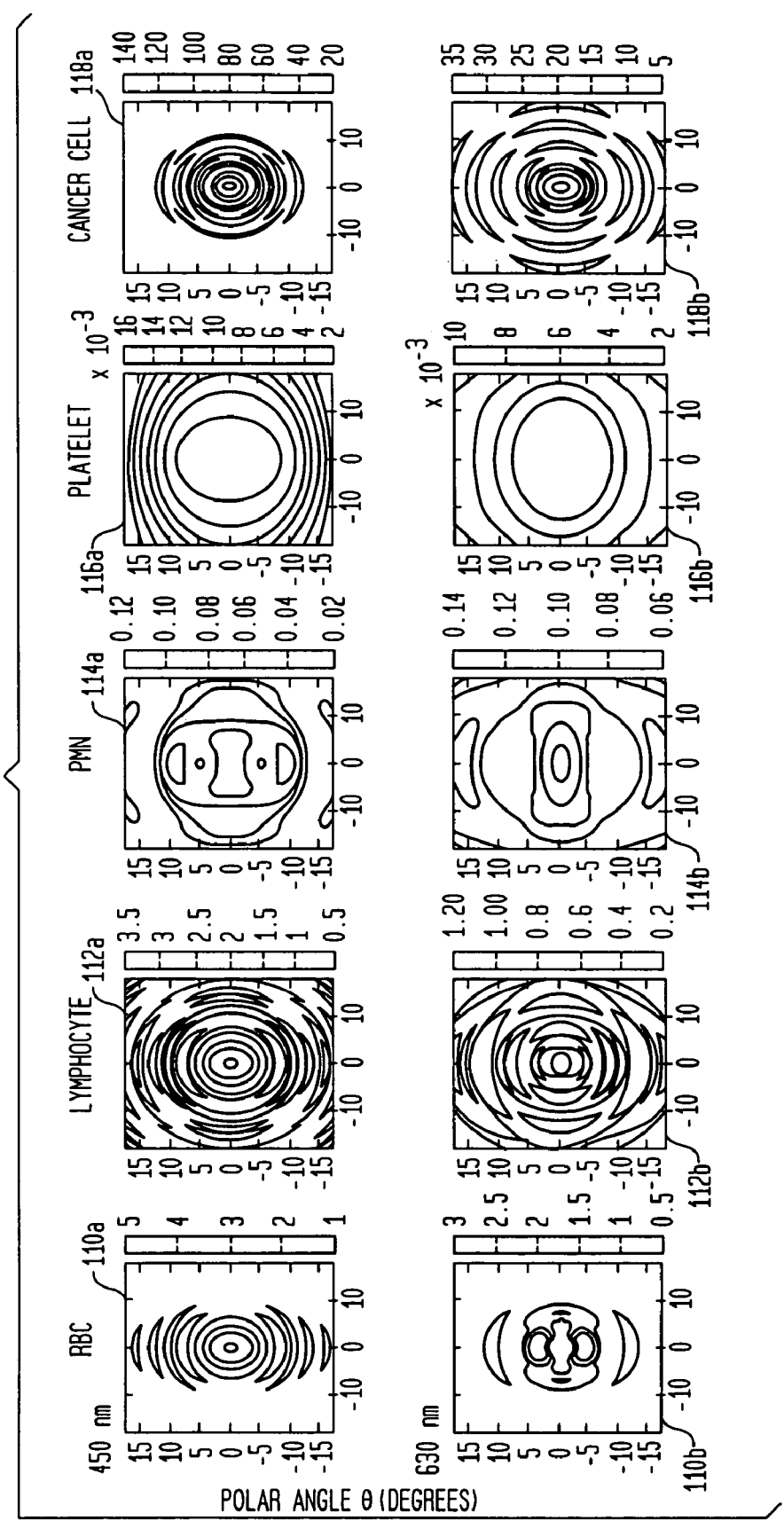
FIG. 5 presents a plurality of theoretical (simulated) backscattered intensity maps corresponding to a variety of cell types, FIG. 6A schematically illustrates a simulated backscattered intensity data and two rectangular slits superimposed over different angular regions of the intensity data over which the data can be integrated to provide a ratio of integrated intensity of the two regions as an indicator of a cell type contributing to the measured backscattering.

To further illustrate the possibility of utilizing differences in the angular distribution of scattered radiation to differentiate among different cell types, FIG. 5 presents expected theoretical (simulated) backscattered intensity maps (graphs) corresponding to a variety of cell types. It should be understood that these graphs are provided for illustration purposes, and actual backscattered intensity data associated with the indicated cell types can be somewhat different that those depicted here. Nonetheless, the presented data indicates that the backscattered angular intensity distributions exhibited by different cell types are significantly dissimilar, and hence can allow differentiating the cell types based on analysis of the backscattered radiation corresponding to different scattering angles and/or different wavelengths.

In particular, intensity maps 110a and 110b, provided as a function of angle $\theta$ ($\theta$=0 corresponds to backscattered light exactly along the optic axis) and angle $\phi$ (in the detection plane), correspond to simulated backscattering maps associated, respectively, with 450 nm and 630 nm excitation wavelengths for a typical red blood cell morphology (particle diameter=7.8 microns; relative refractive index of scattering particle ($n_{rel}$)=1.06; and refractive index of medium ($n_{med}$)=1.33). Further intensity maps 112a and 112b correspond to simulated approximate backscattered intensity by the nucleus of a lymphocyte (particle diameter=10 microns, $n_{rel}$=1.05 and $n_{med}$=1.36) associated with excitations at 450 mm and 630 nm, respectively. Intensity maps 114a and 114b correspond to approximate simulated backscattered intensity from a nuclear lobe of a polymorphonuclear leukocyte, eosinophil or neutrophil (particle diameter=4 microns, $n_{rel}$=1.05 and $n_{med}$=1.36) associated with excitations at 450 nm and 630 nm, respectively.

Moreover, intensity maps 116a and 116b present approximate simulated backscattered intensity from a platelet-like particle (particle diameter=2 microns, $n_{rel}$=1.06 and $n_{med}$=1.36) in response to excitation wavelengths at 450 nm and 630 nm, respectively. And finally, intensity maps 118a and 118b present backscattered intensity data from the nucleus of a cancer cell (diameter=13 microns, $n_{rel}$=1.06 and $n_{med}$=1.36) in response to excitations at 450 nm and 630 nm, respectively. The methods of the invention employ such differences in the backscattered angular intensity distributions to extract information regarding cell types of interest.

By way of example, once the contribution associated with a cell type of interest to the backscattered data is determined, its integrated backscattered intensity can be employed, together with the intensity of the excitation radiation, the duration of exposure of the blood to the excitation radiation, as well as a scattering cross-section of the cell type of interest, to determine a count of that cell type in the subject's blood. The scattering cross-section can be derived, for example, from in-vitro experiments performed on that cell type extracted from blood. Alternatively, a theoretical cross-section calculated based on the shape, the size and internal structure of the cell type can be employed. In some embodiments, a combination of experimentally and theoretically derived scattering cross sections can be utilized.

Moreover, in embodiments in which two or more excitation wavelengths are utilized, the "multi-color" backscattering data can complement the multi-angle data to facilitate detection, differentiation, and counting of one or more cell types of interest. For example, at a given scattering angle, the ratio of scattered intensities corresponding to two wavelengths can be different for two different cell types.

Figure 6A:
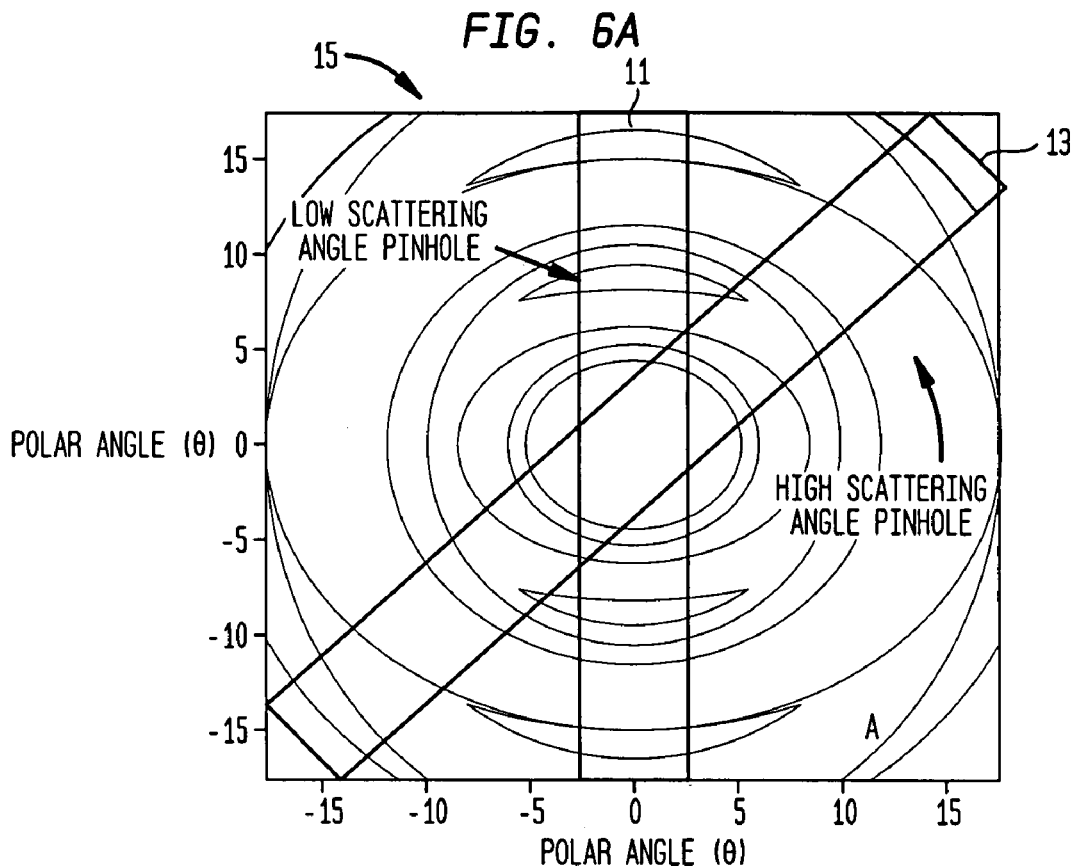
FIG. 6B is a plot depicting an integrated backscattered intensity ratio in the two angular regions of FIG. 6A at one wavelength as a function of a similar ratio at another wavelength for a number of different cell types.
FIG. 6C is a plot depicting an integrated backscattered intensity ratio in one of the angular regions of FIG. 6A at two different wavelengths as a function of a corresponding integrated intensity ratio in another one of the angular regions at the two different wavelengths for a number of different cell types.
Figure 6B:
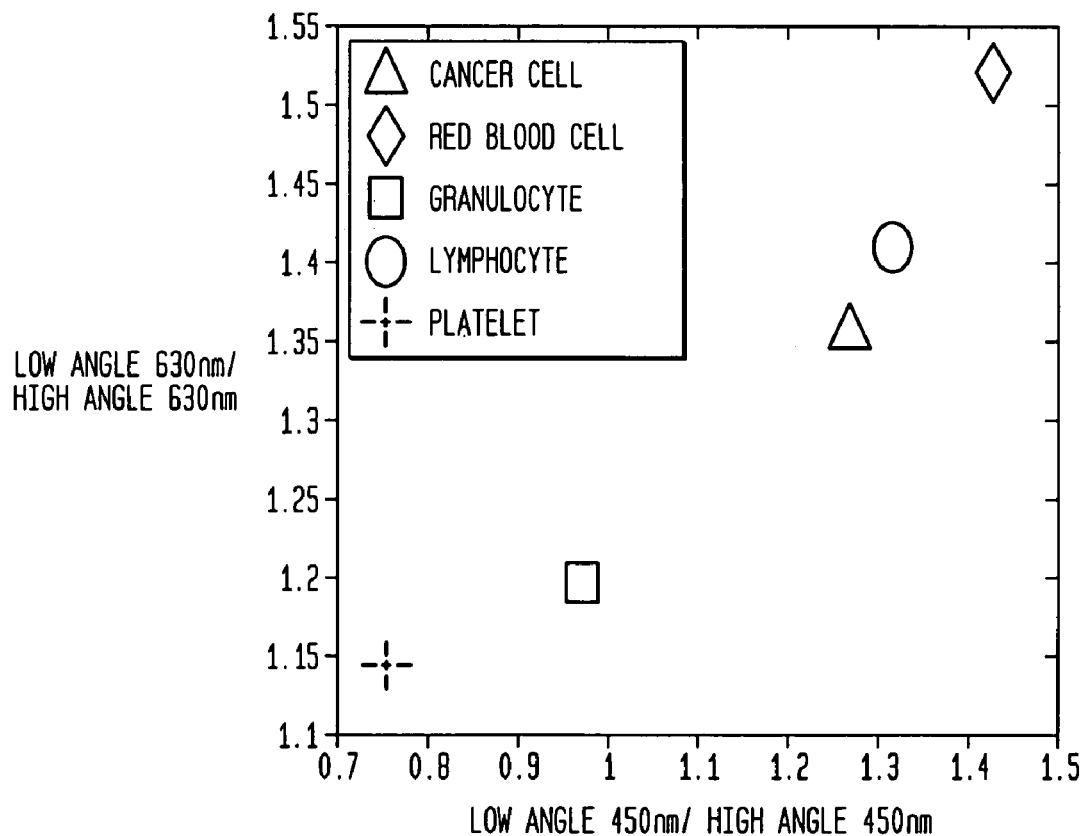

With reference to FIG. 6A, in some embodiments, integrated backscattered intensities within two slits 11 and 13, corresponding to different angular regions within a backscattered intensity map 15 (which is a simulated intensity map and is provided only for illustrative purposes), can be analyzed to determine whether a particular cell type is present in a subject's circulatory system, and if so, to derive selected information regarding that cell type (e.g., its concentration) if desired. For example, FIG. 6B illustrates an exemplary application of this approach to simulated intensity maps for different cell types (cancer cell, granulocyte, red blood cell and platelet). More specifically, FIG. 6B presents a plot of a ratio of the integrated intensity within the slit 13 relative to the integrated intensity associated with the slit 11 at one wavelength (630 nm) as a function of a similar ratio of low-angle (slit 13) relative to high-angle (slit 11) integrated intensity at another wavelength (450 nm) for these cell types based on their simulated backscattered intensity maps.

FIG. 6B shows that the plotted ratios corresponding to one cell type lies in a different location than that associated with another cell type. Hence, such an analysis of integrated intensities at different angular locations and different wavelengths can be utilized, at least as one indicator, for differentiating the contribution of one cell type to the backscattered intensity profile from that of another. FIG. 6C shows a plot of a ratio of the integrated intensity within the slit 13 (low angle) at one wavelength (450 nm) relative to the integrated intensity associated with the slit 11 (high angle) at another wavelength (630 nm) as function of the integrated intensity within the slit 11 (high angle) at one wavelength (450 nm) relative to the integrated intensity within the slit 13 (low angle) at another wavelength (630 nm). Similar to FIG. 6B, the plot of FIG. 6C shows that different cell types lie in different portions of the plot.

Figure 7B:
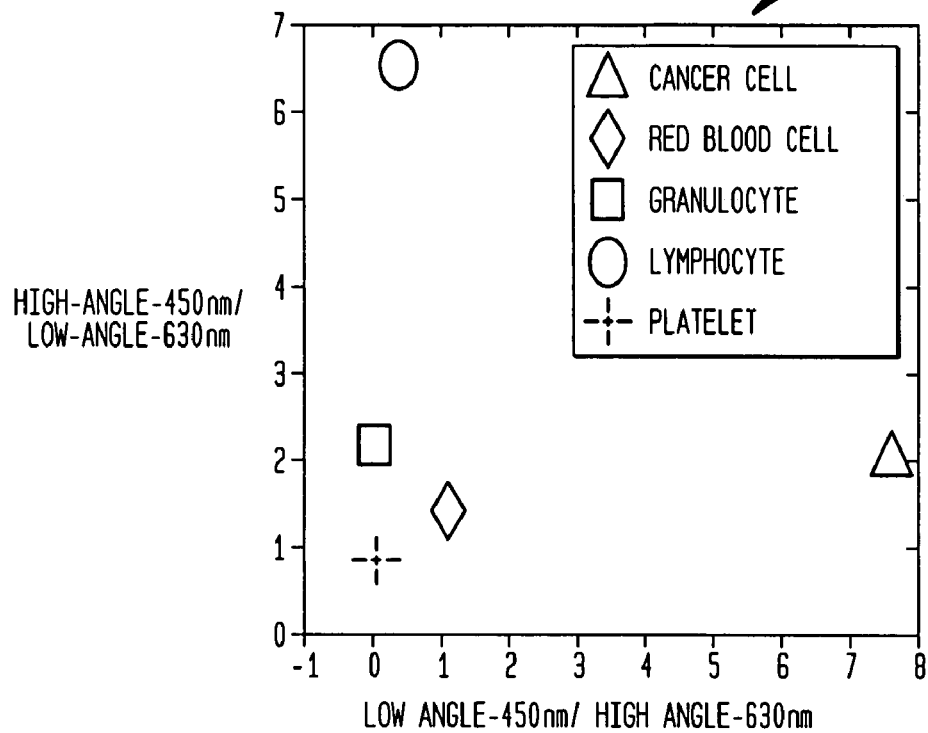
FIG. 7B is a plot depicting an integrated backscattered intensity ratio in one of the angular regions of FIG. 7A at two different wavelengths as a function of a corresponding integrated intensity ratio in another one of the angular regions at the two different wavelengths for a number of different cell types, FIG. 8 schematically illustrates another embodiment of an apparatus for performing in-vivo flow cytometry in accordance with the teachings of the invention, FIG. 9 schematically depicts a transparent microfluidic device that provides a two-dimensional network of capillary channels for fluid flow, and FIG. 10 schematically illustrates various components of a portable device according to one embodiment of the invention for performing in-vivo flow cytometry.

FIG. 7A schematically illustrates that the selected angular regions can have geometrical shapes other than the rectangular shape depicted in FIG. 6A. For example, a ratio of integrated backscattered intensity within two illustrated distinct angular regions 19 and 21 within a backscattered intensity plane 23 (which is a simulated intensity map and is provided only for illustrative purposes) can be employed for differentiating the contribution of one cell type from that of another. For example, FIG. 7B presents a plot 25 of a ratio of high angle (angular region 21) integrated intensity at 450 nm relative to low angle (angular region 19) integrated intensity at 630 nm as a function of a ratio of low angle intensity at 450 nm relative to high angle intensity at 630 m for a plurality of cell types (cancer cell, red blood cell, granulocyte, lymphocyte and platelet), indicating that each cell type is associated with a different location on the plot. Hence, such analysis of the backscattered intensity data can be employed to differentiate one cell type from others.

Figure 8:
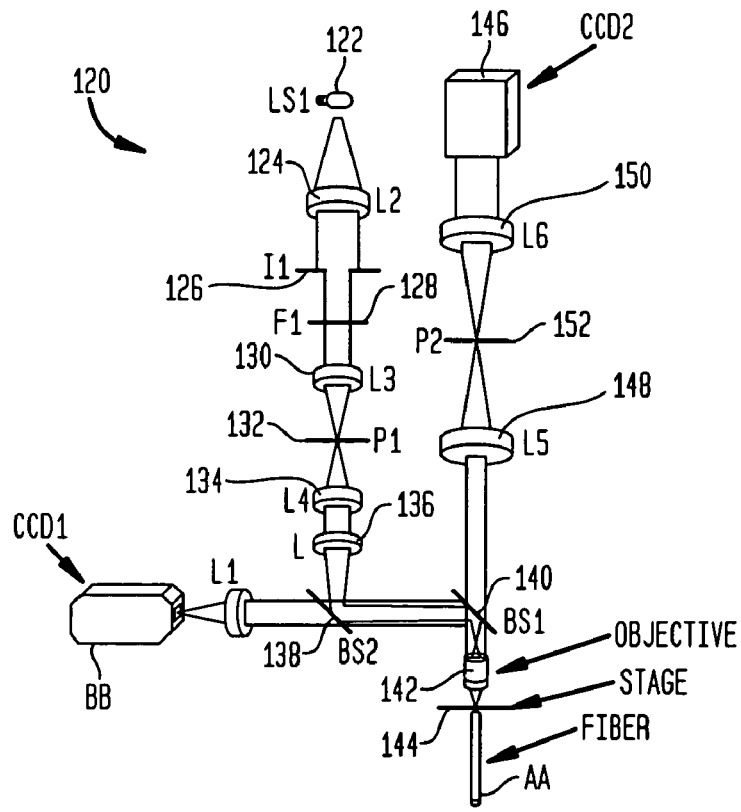

Although in above exemplary apparatus 18 two radiation sources are employed, in other embodiments of the invention, a single radiation source generating two wavelength components of interest, or only a single wavelength component, can be employed to practice the methods of the invention for performing in vivo flow cytometry. By way of example, FIG. 8 schematically illustrates an apparatus 120 according to another embodiment of the invention for performing in-vivo flow cytometry that includes a radiation source 122 generating a relatively broad-band radiation having wavelengths in at least two regions of interest. For example, the source 122 can be a high-power Xenon lamp (e.g., 500 W lamp) whose radiation is collimated by a lens 124, spatially and spectrally filtered, respectively, by an iris 126 and a bandpass filter 128. More specifically, the bandpass filter can select wavelength components within a selected spectral region, e.g., a spectral region ranging from about 600 nm to about 640 nm. An achromat 130 focuses the radiation passing through the bandpass filter onto a pinhole 132, and another achromat 134 collimates the radiation emanating from the pinhole 132 and directs this radiation to an achromat 136. The achromat 136 focuses the radiation, via reflections from beam splitters 138 and 140 onto the back focal plane of an objective lens 142 that in turn collimates the radiation for illuminating blood flowing through a vessel of interest positioned on a stage 144. The illumination of the vessel by a collimated light beam permits more readily defining backscattering angles.

Radiation backscattered from the illuminated blood is collected by the objective lens 142 and a portion of which is directed via transmission through the beam splitter 140 into a detection arm of the apparatus that includes a detector 146, e.g., a CCD camera or a multianode PMT, onto which the scattered radiation is imaged. More particularly, achromats 148 and 150, in conjunction with a pinhole 152, provide spatial filtering of the backscattered light, and image the light onto the CCD. In this embodiment, the pinhole 152 is positioned so as to be confocal relative to the focal plane of the objective so as to substantially reject out-of-focus backscattering light during in vivo measurements. In this manner, a spectroscopic image of the backscattered radiation is obtained at a wavelength region corresponding to scattered radiation generated in response to the wavelength component(s) transmitted through the bandpass filter F1. In some embodiments, this backscattered intensity data is analyzed to recover signatures of one or more cell types of interest to obtain desired information about that cell type, in a manner analogous to those described above. Such analysis of angular dependence of backscattering radiation at a single wavelength component, or a single wavelength region, is herein referred to as "single color" embodiment.

Alternatively, subsequent to obtaining backscattered data in response to excitation radiation corresponding to a wavelength region associated with the filter 128, this filter can be replaced with one having a different transmission spectrum to collect backscattering data in a different wavelength region. In such an embodiment, the angular intensity of the collected backscattered data in both wavelength regions is analyzed, for example, in a manner described above, to derive desired information regarding a cell-type of interest. Simultaneous illumination and detection at more than one wavelength region is also possible with a single broad-band source and an appropriate selection of multi-band filters. This embodiment of the invention is herein referred to as a "multi-color" approach. Those having ordinary skill in the art will appreciate that backscattered data in more than two wavelength regions can also be collected and analyzed according to the teachings of the invention.

As noted above, the methods and systems according to various embodiments of the invention, such as those described above, can be employed to derive, from in-vivo multiple-angle scattering measurements, a count, e.g., relative or absolute, of selected cells, such as cancer cells or white blood cells, in a selected volume of a subject's circulating blood. The angular and/or wavelength regions suitable for detecting cancer cells of a particular type, e.g., prostate cancer, can be in some cases different than the wavelength and/or backscattered angular regions that are suitable for detecting cancer cells of a different type, e.g., leukemic cells.

With continued reference to FIG. 8, in some embodiments of the invention, a vessel of interest can be identified by illuminating tissue containing that vessel by radiation from a source AA (e.g., a ligh-emitting diode) and imaging the transmitted radiation by a lens L1 onto another CCD camera BB.

In some embodiments of the invention, a portion of a vessel having a sufficiently small diameter (e.g., a diameter in a range of about 20 to about 40 microns) is illuminated to ensure that it is very likely that only one cell belonging to a rare cell type of interest (a cell type less ubiquitous than red blood cells, e.g., a white blood cell or a cancer cell) passes at a time through the vessel's illuminated section. The backscattered intensity data at one or multiple wavelengths are analyzed to determine the contribution associated with scattering of radiation by red blood cells. Preferably, backscattered intensity data at two or more wavelengths corresponding to different hemoglobin absorption coefficients (e.g., at a wavelength of 560 nm and a wavelength of 630 nm) are employed for this purpose. Subsequently, the scattering contribution of the red blood cells can be subtracted from the raw backscattering data to obtain a data set that can be analyzed at different angular locations, e.g., in a manner described above, to identify one or more cell types other than the red blood cells flowing through the vessel.

In some embodiments of the invention, in-vitro experiments are performed to determine one or more angular regions that are most suitable for distinguishing a cell type of interest in in-vivo measurements, such as those described above. Such in-vitro experiments can be done statically or dynamically. For example, the apparatus shown above in FIG. 8, and described in detail above, can be utilized to capture backscattered intensity profile of such extracted cells. For example, the cells can be statically placed on the stage 144 and excited by radiation generated by the light source 122. A backscattered intensity map corresponding to such radiation can be captured by the detector 146, e.g., a CCD camera, in a manner discussed above. Such measurements can be performed at single, or preferably at multiple wavelengths. The collected backscattered data can be analyzed to identify the preferred scattering regions, and excitation wavelengths, that can be employed in in-vivo measurements performed in accordance with the teachings of the invention for differentiating that cell type from others. By way of example, step-wise discriminant analysis, well-known to those having ordinary skill in the art, can be employed for this purpose with measured backscattered intensities as a function of wavelength and scattering angle as independent variables and cell type as a dependent variable. Such analysis can also be utilized to estimate the number of cells of a particular cell type that need to be detected at a given signal-to-noise ratio to obtain a certain confidence that cells of that type have been detected. By way of example and only for illustrative purposes, if the objective is to detect cancerous cells of a particular type with a probability of about 20% for false negative and a probability of about $5 \times 10^{-6}$ percent for false positive at a signal-to-noise ratio of about 5, detection of at least two cancer cells can be required.

Figure 9:
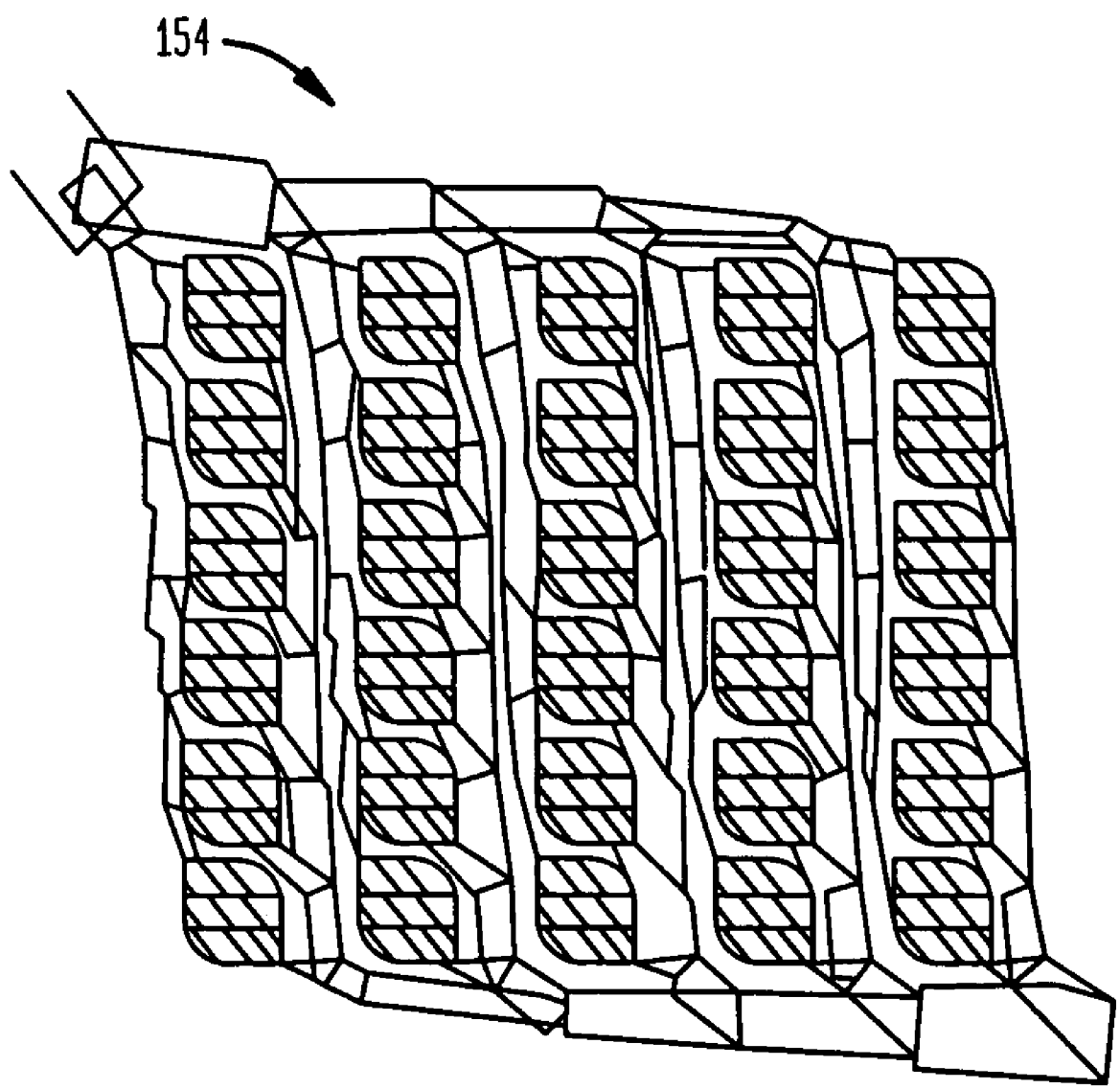

Alternatively, dynamic in-vitro measurements can be performed on cells belonging to a cell type of interest to determine preferred scattering angles and/or excitation wavelengths that can be employed in in-vivo measurements according to the teachings of the invention. For example, with reference to FIG. 9, a transparent microfluidic device 154 providing a two-dimensional network of capillary channels for fluid flow can be employed in such dynamic in-vitro experiments. By way of example, a flow of a fluid sample containing one or more extracted cell types of interest, e.g., a dilute red blood cell sample or one containing neutrophils, lymphocytes, eosinophils, monocytes, basophils or platelets, can be maintained within the microfluidic device. An apparatus according to the teachings of the invention, for example, the above apparatus 120 shown in FIG. 6, can be utilized to focus a beam of light having one or more wavelengths onto a channel of the device for exciting the flowing cells, and obtaining a backscattered intensity map. In this manner, spectroscopic signatures, e.g., the backscattered intensity as a function of scattering angle and excitation wavelength, of each cell type of interest can be characterized for use in in-vivo flow cytometric measurements. In addition, the microfluidic device 154 allows adjusting the flow rate to provide information regarding preferred flow rates for performing in-vivo measurements, e.g., optimal vessel size.

The above in-vitro measurements can be performed on cells extracted from different population groups (e.g., different ethnic and age groups) to provide statistical information that can facilitate analysis of in-vivo backscattering measurements. Moreover, in-vitro experimental measurements, such as those described above, can be combined with simulated backscattering data, such as the data presented in FIG. 5 above, to obtain expected spectroscopic signatures of cell types of interest in the measured backscattered intensity data collected in response to in-vivo excitation.

Figure 10:
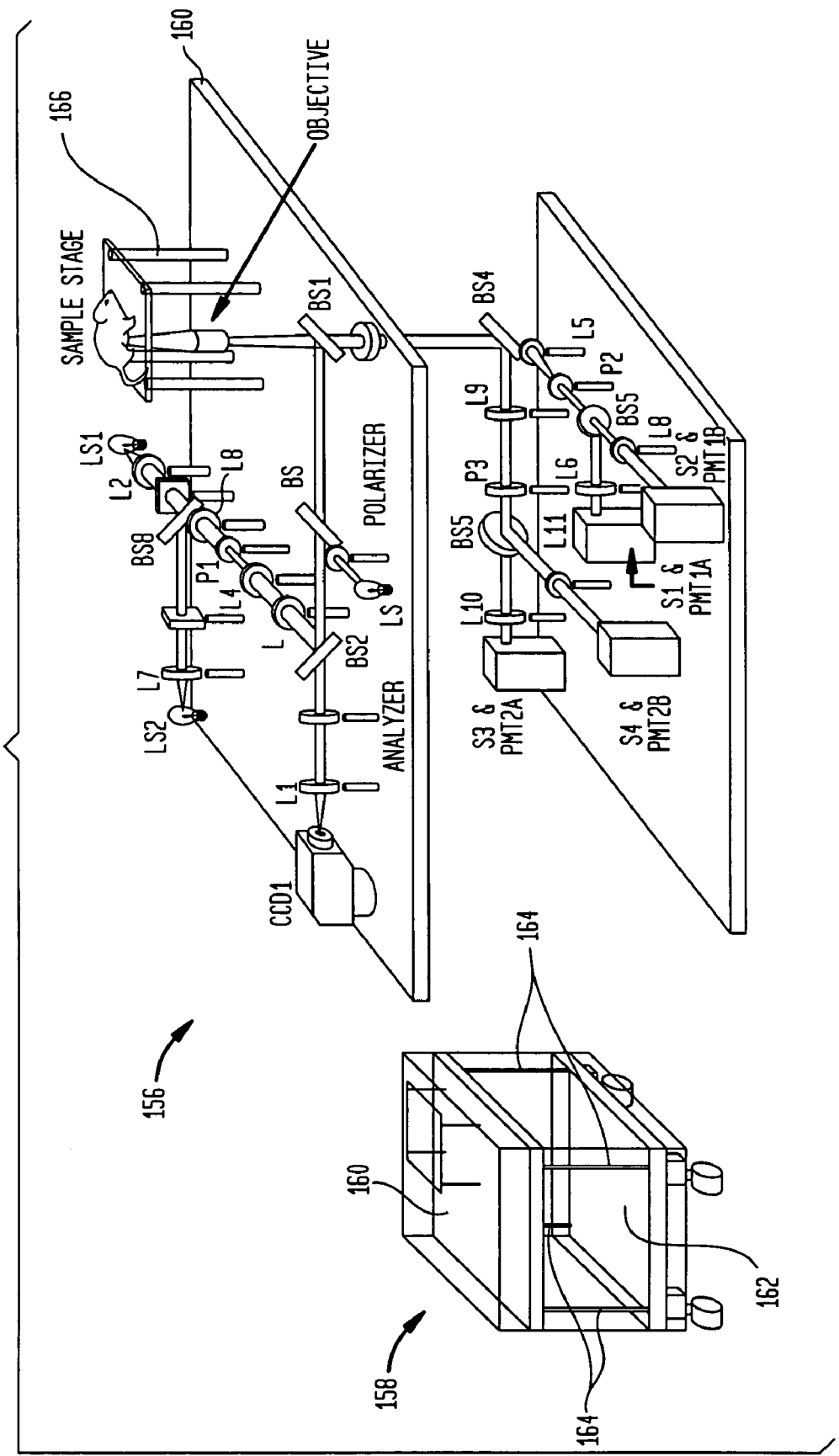

In another aspect, the invention provides a portable device for performing light scattering measurements according to the teachings of the invention, such as those described above, for determining selected cytometric parameters. By way of example, FIG. 10 schematically illustrates various components of such a portable device 156 that includes a portable cart 158 in which two optical breadboards 160 and 162 are mounted. The two breadboards are connected via a plurality of vertical posts 164. Shock absorbers can be coupled to the wheels of the cart to provide further stability, and inhibit frequent misalignment of the optics. In this exemplary embodiment, the optical components for identifying a suitable vessel of a subject (e.g., an animal or a human subject) and for exciting in-vivo blood flowing through that vessel are mounted on the breadboard 160. The subject or a portion thereof can be fixated on a stage 166. A plurality of optical components for detecting the backscattered radiation in different angular regions, and optionally at different wavelengths, are mounted on the breadboard 162. The optical components and their functionality are generally similar to those described in connection with the devices described above with reference to FIGS. 2 and 8. However, in this exemplary embodiment, rather than utilizing a translumination optical system, an orthogonal polarization spectral (OPS) imaging system, well known in the art, can be employed to identify a vessel suitable for performing scattering measurements. Such an optical system can optimize visualization of superficial blood vessels and can enable data acquisition from blood vessels in non-transparent tissues or organs. This can be useful, for example, in acquiring data from blood vessels adjacent to tumors caused by prostate cancer.

Those having ordinary skill in the art will appreciate that various modifications can be made to the above embodiments without departing from the scope of the invention.

What is claimed is:

1. A method of performing flow cytometry, comprising illuminating in vivo a portion of a subject's circulating blood containing at least a cell type of interest with radiation having at least one selected wavelength component, measuring intensity of radiation backscattered from the illuminated blood at at least one angular location, and analyzing said intensity measurements to derive information regarding said cell type.

2. The method of claim 1, wherein said derived information comprises a count of said cell type relative to a count of said cell type measured previously.

3. The method of claim 1, further comprising selecting said wavelength component to be in a range of about 450 nm to about 1000 nm.

4. The method of claim 1, wherein said analyzing step comprises differentiating said cell type from other cells present in said illuminated circulating blood based on said backscattered angular intensity measurements of said at least one wavelength component.

5. The method of claim 1, wherein said cell type of interest is selected from the group consisting of white blood cells, cancer cells, red blood cells, thrombocytes and epithelial cells.

6. The method of claim 1, wherein said step of measuring intensity comprises detecting radiation backscattered from the illuminated blood at said at least one angular location.

7. The method of claim 6, wherein said step of detecting is performed confocally relative to a plane containing a blood vessel illuminated by said radiation.

8. The method of claim 2, wherein said relative cell count can be indicative of progress of a treatment protocol applied to said subject.

9. The method of claim 2, wherein said relative cell count can be indicative of presence of a disease.

10. The method of claim 2, wherein said relative cell count can be indicative of progression of a disease.

11. The method of claim 1, wherein said at least one angular location is selected to lie within a circular strip in a plane of backscattered radiation, said circular strip being delimited by first and second radii relative to an origin of said plane defined as intersection of a central axis of said backscattered radiation with said plane.

12. A method of performing flow cytometry, comprising
illuminating in-vivo a portion of a subject's circulating blood with radiation having at least one selected wavelength component,
detecting intensity of radiation backscattered from the blood in response to said illumination at a plurality of angular locations,
analyzing an angular dependence of said detected backscattered radiation to obtain information regarding at least one cell type in the blood.

13. The method of claim 12, where said analyzing step further comprises differentiating said cell type from at least one different cell type.

14. The method of claim 12, wherein said cell type is selected from the group consisting of white blood cells, cancer cells, red blood cells, thrombocytes and epithelial cells.

* * * * *

UNITED STATES PATENT AND TRADEMARK OFFICE
CERTIFICATE OF CORRECTION

| | | |
|---|---|---|
| PATENT NO. | : 7,264,794 B2 | Page 1 of 1 |
| APPLICATION NO. | : 11/016545 | |
| DATED | : September 4, 2007 | |
| INVENTOR(S) | : Irene Georgakoudi and Charles P. Lin | |

It is certified that error appears in the above-identified patent and that said Letters Patent is hereby corrected as shown below:

Insert the following "Heading" and paragraph before "BACKGROUND OF THE INVENTION" in column 1 line 4:

--FEDERALLY SPONSORED RESEARCH

The invention was made with government support awarded by the National Institutes of Health (NIH) pursuant to Grant Nos. EY14106 and EB000664. The Government has certain rights in the invention.--

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,264,794 B2  Page 1 of 1
APPLICATION NO. : 11/016545
DATED : September 4, 2007
INVENTOR(S) : Irene Georgakoudi and Charles P. Lin It is certified that error appears in the above-identified patent and that said Letters Patent is hereby corrected as shown below:

Col. 1, lines 5 - 8;

Replace paragraph one with the paragraph below:

FEDERALLY SPONSORED RESEARCH

The invention was made with government support awarded by the National Institutes of Health (NIH) pursuant to Grant Nos. EY14106 and EB000664 and by DAMD17-02-2-0006 awarded by the U.S. Department of the Army. The Government has certain rights in this invention.

Signed and Sealed this

Twelfth Day of May, 2009

JOHN DOLL
*Acting Director of the United States Patent and Trademark Office*